US006979462B1

(12) United States Patent
Spireas

(10) Patent No.: US 6,979,462 B1
(45) Date of Patent: Dec. 27, 2005

(54) STABILIZATION OF SOLID DRUG FORMULATIONS

(75) Inventor: Spiridon Spireas, Newtown, PA (US)

(73) Assignee: Mutual Pharmaceutical Co., Inc., Philadelphia, PA (US)

( * ) Notice: Subject to any disclaimer, the term of this patent is extended or adjusted under 35 U.S.C. 154(b) by 269 days.

(21) Appl. No.: 09/690,974

(22) Filed: Oct. 18, 2000

Related U.S. Application Data

(60) Provisional application No. 60/237,442, filed on Oct. 3, 2000.

(51) Int. Cl.[7] ............................................. A61K 9/48
(52) U.S. Cl. ...................... 424/451; 424/452; 424/456; 424/600; 424/725
(58) Field of Search ................................ 424/456, 451, 424/452; 514/21

(56) References Cited

U.S. PATENT DOCUMENTS

| | | | |
|---|---|---|---|
| 4,001,211 A | | 1/1977 | Sarkar .......................... 536/84 |
| 4,389,393 A | * | 6/1983 | Schor et al. |
| 4,983,399 A | | 1/1991 | Maish ......................... 424/465 |
| 5,051,406 A | * | 9/1991 | Satoh |
| 5,225,204 A | | 7/1993 | Chen et al. .................. 424/484 |
| 5,635,209 A | | 6/1997 | Groenewood et al. ....... 424/464 |
| 5,756,123 A | | 5/1998 | Yamamoto et al. .......... 424/451 |
| 5,800,834 A | | 9/1998 | Spireas et al. ............... 424/451 |
| 5,955,105 A | | 9/1999 | Mitra et al. .................. 424/464 |
| 5,958,979 A | | 9/1999 | Lahr et al. ................... 514/567 |
| 5,968,550 A | | 10/1999 | Spireas et al. .............. 424/451 |

FOREIGN PATENT DOCUMENTS

| | | |
|---|---|---|
| EP | 0 707 848 A1 | 4/1996 |
| EP | 0 729 748 A1 | 9/1996 |
| GB | 43 18 577 A1 | 12/1994 |
| WO | WO 87/04342 | 7/1987 |
| WO | WO 95/20953 | 8/1995 |
| WO | WO 97/17951 | 5/1997 |
| WO | WO 01/74448 A1 | 10/1997 |
| WO | WO 97/38960 | 10/1997 |

OTHER PUBLICATIONS

Lieberman, et al.(eds.), Theory & Practice of Industrial Pharmacy, 3rd Ed., Phila., Pa, Lea & Febiger.
Remington's Pharmaceutical Sciences, 18th Ed., Easton, Pa, Mack Publishing Company, 1990.

* cited by examiner

*Primary Examiner*—Shelley A. Dodson
*Assistant Examiner*—Konata M. George
(74) *Attorney, Agent, or Firm*—Woodcock Washburn LLP

(57) ABSTRACT

Pharmaceutical formulations and dosage forms are provided having improved stability to moisture-induced degradation when compared with conventional dosage forms, especially tablets. The invention features low compression forms of drugs known to be susceptible to moisture-induced degradation together with excipients, preferably in encapsulated forms. In other embodiments, relatively non-volatile oils can be admixed with the drug and/or the excipients to stabilize the formulations toward moisture-induced degradation. Hydrophobic powders are also optionally added to the formulations.

28 Claims, No Drawings

STABILIZATION OF SOLID DRUG FORMULATIONS

This application claims priority from U.S. Provisional application Ser. No. 60/237,442, filed Oct. 3, 2000. This application is related to U.S. patent application Ser. No. 09/690,973, filed Oct. 18, 2000.

FIELD OF THE INVENTION

The present invention relates to stable formulations of drugs and methods for producing the same. In particular, the present invention relates to stable formulations of drugs that are susceptible to moisture-induced degradation and methods for producing the same.

BACKGROUND OF THE INVENTION

It is known in the pharmaceutical field that many drugs and classes of drugs exhibit poor or modest shelf stability. For example, a number of solid drug formulations experience such instability that after relatively short periods of time, significant portions of the active materials in the drug have been chemically transformed into other compounds. While such compounds are often relatively benign, occasionally the degradation product or products can either actually comprise an antagonist for the drug or give rise to adverse side effects. In any event, the diminution of desired, active ingredient in such drug formulations is of obvious, deleterious effect, making therapy with such drugs less certain. Accordingly, there is a long-felt need for drug formulations and for unit dosage forms of drugs which experience diminished degradation when compared to typical formulations.

Among the drug classes which are known to be liable to moisture-induced (e.g., hydrolytic) degradation and diminished shelf stability are the thyroid hormones. Thyroid hormones are suitable for therapeutic application in the treatment of hormone disorders. Particularly useful are thyroid hormones of natural or synthetic origin which bear about two or four iodine atoms. Examples of such thyroid hormones are levothyroxine, liothyronin, dextrothyroxine, triiodoacetic acid, thyroglobulin, diiodotyrosine, and analogs and salts thereof.

Levothyroxine is the levo isomer of thyroxine, an active physiological thyroid hormone obtained from the thyroid gland of animals or prepared synthetically. Clinically, levothyroxine is prescribed in thyroid replacement therapy for reduced or absent thyroid function of any etiology, including conditions such as myxedema, cretinism and obesity. Levothyroxine sodium, the sodium salt of levothyroxine, is the preferred form of administration of levothyroxine and is expressed by the chemical formula $C_{15}H_{10}I_4NaO_4 \cdot xH_2O$. It is well known that the stability of levothyroxine is poor it is hygroscopic and degrades rapidly under conditions of high humidity or in the presence of other moisture sources. Levothyroxine also rapidly degrades in the presence of light, under conditions of high temperature, or in the presence of other pharmaceutical excipients, including carbohydrates such as, for example, lactose, sucrose, dextrose and starch, and certain dyes. Accordingly commercially available levothyroxine sodium tablet formulations exhibit a short shelf life.

Thyroid hormones are used therapeutically for thyroid diseases of various origins, including hypothyroidism, hypothyrosis, iodine deficiency and other related secondary diseases. Thyroid hormones are also used prophylactically. Thyroid hormones are used as medicaments and are extremely susceptible to temperature, humidity and oxidation. They are also prone to decomposition by various reaction mechanisms. Additionally, they react with many pharmaceutical excipients which makes it difficult to prepare pharmaceutical formulations containing thyroid hormones which remain effective for a sufficient period of time under regular storage conditions.

Significant efforts have been directed to the development of stable pharmaceutical formulations containing thyroid hormones for use as therapeutic agents. U.S. Pat. No. 5,225,204 (Jul. 6, 1993) is directed to a dosage form containing levothyroxine sodium which includes a stable complex of levothyroxine sodium and a cellulose compound, polyvinylpyrrolidone or a Poloxamer wherein the complex is adsorbed on the surface of a cellulose compound carrier.

U.S. Pat. No. 5,635,209 (Jun. 3, 1997) discloses a medication consisting of the combination of levothyroxine sodium with potassium iodide. This patent further discloses methods for making medication containing levothyroxine sodium comprising combining together levothyroxine mixed with a carrier, potassium iodide mixed with a carrier, a disintegrant, and a lubricant.

U.S. Pat. No. 5,955,105 (Sep. 21, 1999) describes a stable, dosage form pharmaceutical preparation, suitable for the treatment of thyroid disorders, comprising a thyroxine drug, a water soluble glucose polymer, and a partially soluble or insoluble cellulose polymer. This patent also discloses a stable pharmaceutical preparation comprising a thyroxine drug, a water soluble polysaccharide and a partially soluble or insoluble cellulose polymer. This patent further describes a stable pharmaceutical preparation comprising sodium levothyroxine, maltodextrin and microcrystalline cellulose.

U.S. Pat. No. 5,958,978 (Sep. 28, 1999) is directed to stable medicaments containing thyroid hormones wherein the medicament contains sodium thiosulfate as the stabilizing component. This patent also discloses methods for the preparation of stable medicaments comprising adding sodium thiosulfate in a dissolved state to a matrix mixture containing thyroid hormones.

In view of the extreme instability of thyroid hormones, such as levothyroxine, in the presence of moisture, light and heat, there is a long-standing need for stable formulations of thyroid hormones and methods of making such formulations. It is desirable to develop stable thyroid hormone-containing formulations which demonstrate a long enough shelf life for use as therapeutic agents. Also needed are methods for preparing such formulations wherein degradation of the thyroid hormones in the formulations is greatly reduced, thereby providing stable pharmaceutical formulations containing thyroid hormones for use as therapeutic agents in the treatment of disorders associated with reduction or absence of thyroid hormone production Accordingly, it is a principal object of the present invention to provide unit dosage forms of solid drug formulations having a reduced tendency to degrade over time when compared with traditional formulations of such drugs. A further object of the invention is to provide methods of therapy comprising administering to a patient in need of a drug dosage form in accordance with the invention having such diminished tendency to degrade. Another object of the invention is to permit the U.S. and international registration and permission to market certain drug formulations which, absent the stabilization of the present invention, would not be registerable due to an unacceptably high rate of degradation. Other objects will become apparent from a review of the present specification and appended claims.

SUMMARY OF THE INVENTION

The present invention relates to a drug dosage form comprising a compound susceptible to moisture-induced degradation and at least one pharmaceutically acceptable excipient prepared under conditions of low compression. In one embodiment, the compound is subjected to no compression in excess of about 10,000 psi/g, preferably to no compression in excess of about 5,000 psi/g, and more preferably to no compression in excess of about 2,000 psi/g. The formulation of the compound into dosage forms under low compression conditions preferably gives rise to encapsulated forms, such as hydroxypropyl methylcellulose (HPMC) capsules.

In another of its aspects, the present invention relates to a drug dosage form for a compound susceptible to moisture-induced degradation comprising the compound admixed with a substantially non-volatile, pharmaceutically acceptable oil. Suitable oil include animal or vegetable oils such as olive, corn, peanut, nut, soy, rapeseed, cottonseed, vitamin E, fish, or talow-derived oils, mineral oils and silicone oils. The compound—oil admixture is optionally present within a capsule, a soft shell capsule, or a specially sealed hard-shell capsule. The compound—oil admixture is also optionally adsorbed on a pharmaceutically acceptable excipient.

In yet another of its aspects, the present invention relates to a drug dosage form for a compound susceptible to moisture-induced degradation comprising the drug and a pharmaceutically acceptable excipient admixed with a substantially non-volatile, pharmaceutically acceptable oil. Suitable oils include animal or vegetable oils such as olive, corn, peanut, nut, soy, rapeseed, cottonseed, vitamin E, fish, or tallow-derived oils, mineral oils and silicone oils. The excipient—oil admixture is optionally present within a capsule or a tablet.

In still another of its aspects, the present invention relates to a drug dosage form comprising a compound susceptible to moisture-induced degradation admixed with a first pharmaceutically acceptable oil together with a pharmaceutically acceptable excipient admixed with a second pharmaceutically acceptable oil. Suitable first and second pharmaceutically acceptable oils are, independently, an animal or vegetable oil such as olive, corn, peanut, nut, soy, rapeseed, cottonseed, vitamin E, fish, or tallow-derived oil, a mineral oil or a silicone oil.

In a further of its aspects, the present invention relates to a drug dosage form comprising a compound susceptible to moisture-induced degradation and at least one pharmaceutically acceptable hydrophobic powder. In one particular embodiment, the hydrophobic powder is magnesium stearate. Preferably, the hydrophobic powder is triturated directly with the compound.

In still a further of its aspects, the present invention relates to a method for administering a compound susceptible to moisture-induced degradation to a patient comprising providing a unit dose of the compound which has not been processed employing high compression. Alternatively or additionally, the compound and/or the excipient are pretreated with a non-volatile, pharmaceutically acceptable oil.

DESCRIPTION OF PREFERRED EMBODIMENTS

The present invention employs, unless otherwise indicated, conventional methods of chemistry, drug synthesis and formulations, all within the knowledge of those skilled in the art. Such techniques are explained fully in the literature. See, e.g., Remington's Pharmaceutical Sciences, 18th Edition (Easton, Pa.: Mack Publishing Company, 1990), incorporated herein by reference.

In accordance with the present invention, it is alternatively possible either to pretreat a drug, powder excipients, or both with one or more non-volatile, water-immiscible liquids such as oils, and each method of formulations has been found to be beneficial in improving the stability of drugs such as levothyroxine sodium and to form new and useful, solid dosage forms. Without wishing to be bound by theory, the highly desirable stability performance of these new formulations is believed to be based on the fact that the oils are acting as a protective device against extensive contact of the drug with environmental moisture or the equilibrium moisture inherent in mixed powder excipients. In this way, hydrolysis and degradation of the drug in such formulations is significantly reduced.

The present invention may be applied to any of the solid drugs which are known to be subject to moisture-induced degradation in tablet form. Thus, the thyroid hormones such as levothyroxine, ACE-inhibitors such as quinapril, cyclic amino acids such as gabapentin, cholesterol lowering agents such as statins (e.g., lovastatin), non-steroidal anti-inflammatory agents such as aspirin, peptides, and proteins such as insulin, anticancer and oncology drugs such as methotrexate, steroids, and steroidal esters such as methylprednisone sodium succinate, antibiotics such as mitomycin C, nystatin, Rifampin, and others, other cardiac drugs such as nitroglycerin and dioxin, and other drug classes may benefit from the present invention, and its application to all such classes is contemplated hereby. Additionally, in one particular embodiment, the drug is optionally purified prior to use.

The phrase "moisture-induced degradation" as used herein includes, but is not limited to, drug degradation due to hydrolysis only. Instead, the phrase "moisture-induced degradation" also includes any other type of degradation pathway such as oxidation, photodegradation, cyclization, and even dehydration due to ionic attractions, which may be induced or catalyzed by moisture. Thermal degradation initiated by compression and facilitated by moisture is also included in the above phrase.

The term "excipient" as used herein includes, but is not limited to, the family of modified celluloses (e.g., carboxymethyl and ethyl cellulose, hydroxymethyl and ethyl cellulose, microcrystalline cellulose and others), amorphous silicon dioxide, magnesium stearate, starch, sodium starch glycolate, or a combination thereof. In one embodiment, the excipient is at least one of microcrystalline cellulose, starch, and sodium starch glycolate.

Microcrystalline cellulose is known per se and a variety of such are commercially available. Exemplary among these is the family of products sold by the FMC corporation under the trademark Avicel®. Any of the members of this family may be used in connection with the practice of one or more embodiments of the present invention and all are contemplated hereby. Other cellulose products which are similar in nature to microcrytalline cellulose may find utility herein, such a parenchymal cell cellulose.

In addition to the preferred microcrystalline celluloses and similar materials, other cellulosic materials may also be employed in connection with one or more embodiments of the present invention. Thus, modified celluloses such as methyl cellulose, hydroxyethyl cellulose, hydroxypropyl cellulose, methylhydroxyethyl cellulose, methylhydroxypropyl cellulose, carboxymethyl cellulose salts and esters, (e.g. sodium, potassium etc. salts), and other cellulose derivatives may be so employed. It will be appreciated by persons of ordinary skill in the art that such cellulosic materials should be consistent with the overall spirit of the invention. Thus, such materials may be employed which do not adversely effect the processing set forth herein and which do not interfere with the stability of the resulting products.

Particularly useful non-volatile, water-immiscible liquids include oils such as olive, corn, peanut, nut, soy, rapeseed, cottonseed, vitamin E, fish, tallow-derived or other oils. The oil may also be a mineral oil, silicone oil or the like and may be present as a mixture of oils. By "non-voltile3[ it is meant that the oils have a relatively low vapor pressure at conventional temperatures and other conditions. Oils such as the essential oils which have relatively high vapor pressures (e.g., aromatic constitutives) are not preferred for this application, although some of such species may find some utility herein.

In accordance with these aspects of the invention, drug and oil are combined in any ratio which gives rise to the beneficial properties desired. Conveniently, drug and oil can be combined in ratios of about 1:1 to about 1:5000 or more, weight to weight. Ratios of from about 1:40 to about 1:400 are more preferred. When the oil is admixed with excipient, ratios of excipient to oil of from about 1:1 to about 1:5000 or more are also conveniently used with ratios of from about 1:40 to about 1:400 being preferred. Other ratios may also be used, especially when both drug and excipient are admixed with oils.

The drug and/or excipients are mixed with the non-volatile, water-immiscible liquids using any of a variety of conventional techniques. For example, when the excipients are to be pretreated, the liquids can be dissolved in a solvent (e.g., acetone) and the resulting solution used to granulate the excipients. When the drug is to be pretreated, the drug can be suspended directly in the liquids and homogenized to form a drug/liquid suspension.

A further way has also been found to greatly reduce unwanted moisture-induced degradation in drugs. For example, with respect to levothyroxine, it has now been surprisingly discovered that an important factor which can be used to achieve stable powder formulations of levothyroxine and other solid drugs which can experience undesired rates of moisture-induced degradation, is the avoidance of high degrees of compression. Without being bound by theory, it has now been found that when a powder formulation comprising levothyroxine mixed with pharmaceutically acceptable powder excipients is compressed into tablets, some of the equilibrium moisture inherently possessed by such inert powder excipients is squeezed out of the interior bulk of the powder particles to the exterior surfaces of the powder particles; those surfaces being in contact with the drug particles. Such drug-moisture contact is believed to result in initializing at a relatively high rate, the hydrolysis of levothyroxine to its degradation products.

It has actually been reported that the degradation of levothyroxine from highly compressed systems, i.e., tablets, is biphasic wherein, at a first stage immediately after compression into tablets, the drug degrades at a much higher rate as compared to a second, slower degradation stage. It has now been found that the drug degradation stage occurring immediately after compression is associated with the aforementioned contact of the drug particles with the equilibrium inherent moisture squeezed onto the particle surfaces of the inert powder excipients included in the tableting mixture. Several commonly used and pharmaceutically acceptable powder excipients may possess inherent moisture levels equivalent of up to 10% of their weight. It is desired to continue to use such excipients, however, especially those with moisture contents of 5% and even 10% by weight. Thus, the compression of such materials can force very significant amounts of moisture onto the surfaces of such particles with the attendant, rapid moisture-induced degradation of drugs in contact with such compressed particles.

Accordingly, it has now been found that provision of levothyroxine in dosage forms which are highly compressed, such as tablets, should be avoided when neither the drug nor the excipients are pretreated as described above. Rather, in accordance with the invention, the drug is preferably provided in unit dosage forms in which the drug has not been compressed in the presence of moisture-containing excipients to a degree such that moisture is exuded onto the surfaces of the excipient particles. For example, a hard-shell capsule of levothyroxine, in which the powder mixture is not strongly compressed exhibits very greatly improved stability to moisture-induced degradation as compared to previously available, highly-compressed tablets of the drug.

It is also known that cyclic amino acids of the general formula:

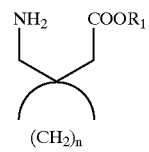

wherein $R_1$ is H or a lower alkyl radical and n is 4, 5, or 6, are subject to degradation during storage. The degradation is believed to be due, at least in part, to conversion of the cyclic amino acid to its lactam form:

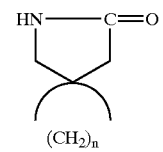

Cyclization of the amino acid to form the lactam impurity results in the loss of water. The cyclization is believed to be catalyzed by highly ionized, electronegative anion impurities (e.g., $Cl^-$). Pretreatment of the amino acid and/or the excipients with which it is compounded in accordance with the present invention is expected to serve to isolate the amino acid from the anion impurities, thereby stabilizing the amino acid relative to its lactam form.

In addition, ACE inhibitors, or inhibitors of Angiotensin Converting Enzymes, are drugs useful in the treatment of cardiovascular disorders, especially hypertension. ACE inhibitors include, but are not limited to, enalapril maleate and similar salts; quinapril hydrochloride and similar salts; benazepril hydrochloride and similar salts; moexipril hydrochloride and similar salts; lisonopril hydrochloride and similar salts; ramipril hydrochloride and similar salts; and indopril hydrochloride and similar salts. Typical breakdown products of ACE inhibitors include, but are not limited to, enalaprilat and/or enalapril-diketopiperazine (DKP) for enalapril species, quinaprilat and/or quinapril-DKP for quinapril drugs, and other breakdown products well-known to those of skill in the art.

However, it has been widely observed that ACE inhibitors are susceptible to breakdown, especially due to degradation and/or cyclization between the time of manufacture and the time of desired usage. Breakdown of ACE inhibitors has been found to occur both in solid and in liquid states. Such breakdown is due, at least in part, to hydrolysis of the drug by water. As breakdown of ACE inhibitor increases, the concentration of available, functional ACE inhibitor decreases. Also, at least some of the degradation products of such breakdown are believed to be deleterious. Accordingly, such breakdown is to be avoided. It is expected that the moisture-induced hydrolysis of ACE inhibitors can be reduced by pretreating the drug and/or the excipients with which it is compounded in accordance with the present invention.

Persons of ordinary skill in the pharmaceutical formulation art will recognize that the present invention distinguishes between highly compressed drug forms and unit dosages and such forms and dosages which have not been highly compressed. It is believed that the relationship between the compression of solid forms of drugs susceptible to moisture-induced degradation and the rate of or tendency toward such degradation for such drugs has not been appreciated heretofore. For purposes of this invention, the degree of compression can be defined functionally. Thus, a drug form or unit dosage has been "highly compressed" if the amount of pressure applied to the form or dosage is such as to exacerbate the moisture-induced degradation of the drug comprising the form or dosage. This amount of compression can vary with the identity of drug, excipient and other factors. However, it is believed that no more than ordinary skill and routine evaluation is needed to determine whether the foregoing conditions have been met with respect to any particular drug composition, form, formulation or unit dose. Without departing from the generality of the foregoing, it is believed that compression in excess of about 10,000 pounds per square inch per gram of compacted mass (psi/g), preferably about 5,000 psi/g and still more preferred about 2,000 psi/g should be avoided in such processing. For the purposes of the present invention, formulation of drug forms, dosage forms and the like with the avoidance of compression in excess of about 10,000 psi/g or which otherwise avoids the above-described exacerbation of moisture-induced degradation of drugs which are susceptible to such degradation is referred to as "conditions of low compression."

As used herein, the terms "dosage form," "pharmaceutical dosage form," "pharmaceutical formulation," and "pharmaceutical preparation" refer to the final solid pharmaceutical product. These terms include, but are not limited to, tablets included molded tablets, caplets, beads, wafers, and capsules (including both hard shell capsules and soft gelatin capsules). These terms also refer to liquisolid systems which are flowing and compressible powdered forms of liquid medications. The processes of preparing pharmaceutical preparations and dosage forms are well known to those of skill in the art. See, e.g., Theory & Practice of Industrial Pharmacy, 3$^{rd}$ Edition, Liberman, Lachman, and Kanig, eds. (Philadelphia, Pa.: Lea & Febiger) incorporated herein by reference.

The formulation of solid drugs into dosage forms under low compression conditions may conveniently and preferably give rise to encapsulated forms. Hard shell capsules filled with low compression powdered drug composition are most convenient; their manufacture and processing is well-known and routine. A particularly preferred capsule shell type is one comprising hydroxypropyl methylcellulose (HPMC), although all capsule forms may beneficially be used in conjunction with this invention. Other capsule shells, such as those consisting of polyethylene glycols or other cellulosic derivatives may also be advantageously used herein.

Other examples of solid dosage forms which do not require high-compression conditions during their preparation are pellets, beads, liquisolid systems, soft gelatin capsules containing liquid, specially-sealed hard-shell capsules containing liquid, molded tablets, wafers, etc.

A "liquisolid system" refers to formulations formed by conversion of liquid drugs, drug suspensions or drug solutions in non-volatile solvents into dry, nonadherent, free-flowing and compressible powder admixtures by blending the suspension or solution with selected carriers and coating materials. Based upon the type of liquid medication contained, liquisolid systems are classified into three categories: (I) powdered drug solution (containing a drug solution); (ii) powdered drug suspension (containing a drug suspension); and (iii) powdered liquid drug (containing a liquid drug). Liquisolid systems are described in U.S. Pat. Nos. 5,968,550 and 5,800,834, each of which is incorporated herein by reference in its entirety. It will be appreciated that such liquisolid systems may be prepared in accordance with the present invention and that the same is within the spirit hereof. Although not generally preferred, when the drug and/or excipients are pretreated with a water-immiscible liquid in accordance with the present invention, liquisolid powder systems can be also compressed into tablets. Such tablets posses stability properties superior to those of commercial products.

Significant stability enhancement benefits of premixing the drug with some traditionally hydrophobic powders have also been discovered as a way to reduce unwanted moisture-induced degradation in drugs. The hydrophobic powders are preferably triturated directly with the drug. In one particular embodiment, the hydrophobic powders are triturated directly with the drug prior to blending the drug with other powder excipients, including powder excipients previously admixed with a non-volatile oil. Suitable hydrophobic powders include, but are not limited to, lubricants such as magnesium stearate, antioxidants, other solid waterproofing agents, and combinations thereof. It would be appreciated by those skilled in the art that this method can be used in various intensities and in combination with one or more of the other methods described herein. However, it is well known that extensive use of such hydrophobic powders (i.e., magnesium stearate) may deleteriously affect the dissolution of drugs in aqueous media by waterproofing the drugs to irreversible levels. Accordingly, the use of hydrophobic powders should be optimized to also maintain acceptable drug dissolution properties.

As used herein, "substantially free" refers to compositions that have significantly reduced levels of detectable breakdown products or degradation products. The terms "breakdown products" and "degradation products" refer to undesired contaminants formed by the decomposition or degradation of the thyroid hormone. Decomposition or degradation of thyroid hormone may be caused by exposure of the thyroid hormone to moisture, heat or light.

By "pharmaceutically acceptable" or "pharmacologically acceptable" is meant a material which is not biologically or otherwise undesirable, i.e., the material can be administered to an individual along with the stabilized drug formulation without causing any undesirable biological effects or interacting in a deleterious manner with any of the components of the formulations in which it is contained.

EXAMPLES

Drug formulations in accordance with the present invention were prepared and tested as follows. Powder formulations having the composition of Example No. 1 listed in Table 1a was prepared by pretreating the drug with oil (the "drug-oil-pretreament" method). Accordingly, the drug was suspended in oil and homogenized to form a drug/oil suspension. The drug/oil suspension was then incorporated onto a powder carrier comprising microcrystalline cellulose and hydroxypropyl methylcellulose. The resulting wet liquid/powder admixture was then mixed with fine silicon dioxide particles to produce a free-flowing and readily compressible liquisolid system. A disintegrant, sodium starch glycolate, and a lubricant, magnesium stearate, were then mixed with the liquisolid powders to produce the final powders.

Powder formulations having the compositions of Example No. 2-7 listed in Table 1a were prepared by pretreating the excipient with oil (the "excipient-oil-pretreatment" method). Accordingly, the oil was dissolved in acetone and the resulting solution was used to granulate the inactive powder excipients (i.e., hydroxypropyl methylcellulose, microcrystalline cellulose, and amorphous silicone dioxide, blended together). After drying, the oil-treated excipients were mixed with levothyroxine and encapsulated in HPMC capsules to produce the final product A first aliquot (about 1 kg) of each formulation was then compressed into tablets. A second aliquot of each formulation was encapsulated in gelatin capsules. A third aliquot of each formulation was encapsulated in hard-shell HPMC capsules. All unit doses contained 0.025 mg of levothyroxine. Samples of each of the tablets and capsules were then stored at 60° C. and a relative humidity of 75% for 4–6 days. At the end of the desired storage time, the extent to which the drug had degraded was determined as the percent decrease in the weight of the drug (% Degradation={([initial weight of drug in mg]−[final weight of drug in mg])×100}/[0.025 mg]. The % Degradation data is shown in Table 1b. For comparison purposes, when tablets of a commercial product (Synthroid 0.025 mg; Lot #000090074, Expiration date: April 2002) were stored under the same conditions for 5 days, the tablets showed a degradation of 36.7%.

TABLE 1a

| Ingredient | Example No. | | | | | | |
|---|---|---|---|---|---|---|---|
| (mg per unit dose)* | 1 | 2 | 3 | 4 | 5 | 6 | 7 |
| levothyroxine sodium | 0.025 | 0.025 | 0.025 | 0.025 | 0.025 | 0.025 | 0.025 |
| olive oil | 10 | 5 | 3 | — | 5 | 5 | 1.4 |
| soybean oil | — | — | — | 2 | — | — | — |
| acetone[a] | — | 40 | 40 | 40 | 40 | 20 | 56 |
| hydroxypropyl methylcellulose | 20[b] | 20[b] | 10[c] | 10[c] | — | 10[c] | 14.1[c] |
| amorphous silicon dioxide[d] | 11 | 15 | 15 | 15 | 15 | 8 | 21.1 |
| microcrystalline cellulose[e] | 144 | 150 | 150 | 150 | 150 | 80 | 210.9 |
| sodium starch glycolate[f] | 23 | — | — | — | — | — | — |
| magnesium stearate | 2 | — | — | — | — | — | 2.5 |

*As weighed prior to manufacturing.
[a]Not present in final product.
[b]Methocel K100LV.
[c]Methocel K100M.
[d]Syloid 244 FP.
[e]Avicel PH 200.
[f]Explotab.

TABLE 1b

| | | Example No. | | | | | |
|---|---|---|---|---|---|---|---|
| | | 1 | 2 | 3 | 4 | 5 | 6 | 7 |
| storage time (days) | | 4 | 6 | 5 | 5 | 5 | 5 | 5 |
| % Degradation[a] | gelatin capsule | 12.1 | 20.8 | 22.7 | — | — | — | — |
| | HPMC capsule | 6.5 | 11.3 | 5.9 | 8.7 | 7.2 | 4.2 | 16.0 |
| | tablet | 26.1 | 30.3 | — | 14.0 | 17.6 | 18.5 | 25.7 |

[a]Results reported as percent of drug degraded after storage at 60° C. and 75% relative humidity.

The data of Table 1b show that the most stable products were the HPMC capsules followed by the gelatin capsules. The highly compressed tablet forms presented, in a significant and consistent manner, the worst stability characteristics. For example, when a powder formulation of levothyroxine sodium (Example No. 1) was compressed into tablets, the tablets presented 26.1% degradation after storage for 4 days at 60° C. and 75% relative humidity. On the other hand, when the same powder system was encapsulated under low compression conditions in hard-shell capsules consisting of gelatin or HPMC, they degraded only 12.1% or 6.5%, respectively, at the same storage conditions.

The data of Table 1b also show that pretreated liquisolid powder systems can be compressed into tablets. Such tablets posses stability properties superior to those of commercial products. For example, when stored for 5 days at 60° C. and 75% relative humidity, optimized liquisolid tablet of Levothyroxine Sodium (Example No. 4) degraded at a level of only 14%, whereas the market-leading Synthroid 0.025 mg Tablets (Lot: 000090074, Exp.: April 2002) displayed a 36.7% degradation at the same storage conditions.

Stability results of levothyroxine liquisolid formulations encapsulated in hard-shell HPMC capsules and prepared by pretreating the excipient with oil (the "excipient-oil-pretreatment" method) are shown in Table 2. The oil was dissolved in acetone and the resulting solution was used to granulate the inactive powder excipients (i.e., microcrystalline cellulose and amorphous silicone dioxide, blended together). After drying, the oil-treated excipients were mixed with levothyroxine and encapsulated in HPMC capsules to produce the final product. Several batches of 2–3 kg were prepared using this methodology and scalable equipment such as a Collette 10 L granulator.

The data of table 3 show that optimized capsule formulations of levothyroxine made with levothyroxine that has been previously treated and waterproofed with oils can give increased stability properties as compared to commercial products Stability results of a levothyroxine liquisolid formulation encapsulated in hard-shell HPMC capsules and prepared by combining the excipient-oil-pretreatment and the drug-oil-pretreatment methods are shown in Table 4. Oil was dissolved in acetone and the resulting solution was used to

TABLE 2

| Example No. | | 8 | 9 | 10 | 11 | 12 | 13 |
|---|---|---|---|---|---|---|---|
| Ingredient | levothyroxine sodium | 0.025 | 0.025 | 0.025 | 0.025 | 0.025 | 0.025 |
| (mg per unit dose)* | olive oil | 1.0 | 0.5 | 1.5 | 0.2 | 0.8 | 1.0 |
| | acetone[a] | 25 | 25 | 25 | 25 | 25 | 25 |
| | amorphous silicon dioxide[b] | 9.0 | 9.0 | 9.0 | 9.0 | 9.0 | 9.0 |
| | microcrystalline cellulose[c] | 90 | 90 | 90 | 90 | 90 | 90 |
| % Degradation[d] | | 7.0 | 6.8 | 5.2 | 8.9 | 7.7 | 8.4 |

*As weighed prior to manufacturing.
[a]Not present in final product.
[b]Avicel PH 200.
[c]Explotab.
[d]Reported as the percent of drug degraded after storage at 60° C. and 75% relative humidity for 5 days.

The data of Table 2 show that optimized capsule formulations of levothyroxine made with powder excipients that have been previously treated and waterproofed with oils can give increased stability properties as compared to commercial products.

Stability results of levothyroxine liquisolid formulations encapsulated in hard-shell HPMC capsules and prepared by pretreating the drug with oil (the "drug-oil-pretreatment" method) are shown in Table 3. The drug was suspended in oil and homogenized to form a drug/oil suspension. The drug/oil suspension was then incorporated onto a powder carrier comprising microcrystalline cellulose and hydroxypropyl methylcellulose. The resulting wet liquid/powder admixture was then mixed with fine silicon dioxide particles to produce a free-flowing and readily compressible liquisolid system. A disintegrant, sodium starch glycolate, and a lubricant, magnesium stearate, were then mixed with the liquisolid powders to produce the final powders, which were encapsulated in hard-shell HPMC capsules. Several batches of 2–3 kg each were prepared using this methodology and scalable equipment.

granulate and pretreat the inactive powder excipients (microcrystalline cellulose and silicon dioxide), as described above in connection with the formulations of Table 2. Additionally, the drug was suspended in oil, as described in connection with the formulations of Table 3. The dried oil-treated excipients were then mixed with the drug/oil suspension to yield a free-flowing and readily compressible liquisolid system. Magnesium stearate, a lubricant, was also added to produce the final powder, which was encapsulated into hard-shell HPMC capsules.

TABLE 4

| | Example No. | 20 |
|---|---|---|
| Ingredient | levothyroxine sodium | 0.025 |
| (mg per unit dose)* | olive oil (for drug) | 3 |
| | olive oil (for excipient) | 1 |
| | acetone[a] | 40 |
| | amorphous silicon dioxide[b] | 22 |

TABLE 3

| Example No. | | 14 | 15 | 16 | 17 | 18 | 19 |
|---|---|---|---|---|---|---|---|
| Ingredient | levothyroxine sodium | 0.025 | 0.025 | 0.03 | 0.025 | 0.025 | 0.025 |
| (mg per unit dose)* | olive oil | 10 | 10 | 15 | 15 | 5 | 5 |
| | hydroxypropyl methylcellulose[a] | 10 | — | 6 | 6 | 6 | 16 |
| | amorphous silicon dioxide[b] | 11 | 11 | 16 | 16 | 16 | 16 |
| | microcrystalline cellulose[c] | 144 | 144 | 144 | 144 | 144 | 144 |
| | sodium starch glycolate[d] | 23 | 23 | 17 | 17 | 17 | 17 |
| | magnesium stearate | 2 | 2 | 2 | 2 | 2 | 2 |
| % Degradation[e] | | 17.6 | 15.5 | 10.8 | 15.0 | 12.6 | 18.6 |

*As weighed prior to manufacturing.
[a]Methocel K100LV.
[b]Syloid 244 FP.
[c]Avicel PH 200.
[d]Explotab.
[e]Reported as the percent of drug degraded after storage at 60° C. and 75% relative humidity for 5 days.

TABLE 4-continued

| | Example No. | 20 |
|---|---|---|
| | microcrystalline cellulose[c] | 224 |
| | magnesium stearate | 2 |
| % Degradation[d] | | 11.9 |

*As weighed prior to manufacturing.
[a]Not present in final product.
[b]Syloid 244 FP.
[c]Avicel PH 200.
[d]Reported as the percent of drug degraded after storage at 60° C. and 75% relative humidity for 5 days.

The data of Table 4 show that a combination of drug-oil-pretreatment and excipient-oil-pretreatment can give increased stability properties as compared to commercial products.

Significant stability enhancement benefits of premixing the drug with some traditionally hydrophobic powders such as the lubricant magnesium stearate have also been discovered. In general, the use of antioxidants and other solid waterproofing agents in combination with the above methods may be also beneficial. As shown in Table 5, improved stability of levothyroxine is also obtained when the drug is pretreated with a hydrophobic solid powder (the "hydrophobic-powder-waterproofing" method). Accordingly, the drug was first mixed with a hydrophobic powder, magnesium stearate, at various levels. The other powder excipients were then blended in. Several pilot batches of 2–3 kg each were prepared using this methodology and scalable equipment.

TABLE 5

| Example No. | 21 | 22 | 23 | 24 |
|---|---|---|---|---|
| Ingredient (mg per unit dose)* | | | | |
| levothyroxine sodium | 0.025 | 0.025 | 0.025 | 0.025 |
| hydroxypropyl methylcellulose[a] | 20 | 10 | 10 | 10 |
| amorphous silicon dioxide[b] | 14 | 15 | 15 | 15 |
| microcrystalline cellulose[c] | 150 | 150 | 150 | 150 |
| magnesium stearate | 10 | 5 | 2.5 | 1.0 |
| % Degradation[d] | 0 | 5.9 | 3.9 | 9.5 |

*As weighed prior to manufacturing.
[a]Methocel K100M.
[b]Syloid 244 FP.
[c]Avicel PH 200.
[d]Reported as the percent of drug degraded after storage at 60° C. and 75% relative humidity for 5 days.

The data of Table 5 show that superior stability properties are obtained for the formulations made according to the hydrophobic-powder-waterproofing method.

While the present invention has been described in accordance with certain of its preferred embodiments, it is not to be construed as limited thereto.

What is claimed is:

1. A drug dosage form prepared by compression techniques comprising:
    a substantially non-volatile, pharmaceutically acceptable oil, and
    a compound susceptible to moisture-induced degradation treated with the substantially non-volatile, pharmaceutically acceptable oil to substantially waterproof the compound susceptible to moisture-induced degradation;
    the drug dosage form prepared by:
    (a) dispersing the compound susceptible to moisture-induced degradation in the substantially non-volatile, pharmaceutically acceptable oil; and
    (b) compacting the compound susceptible to moisture-induced degradation into dosage forms using compression pressures of up to 5,000 psi/g.

2. The drug dosage form of claim 1 wherein the oil is an animal or vegetable oil.

3. The drug dosage form of claim 1 wherein said oil is olive, corn, peanut, nut, soy, rapeseed, cottonseed, vitamin E, fish, or tallow-derived oil.

4. The drug dosage form of claim 1 wherein the oil is a mineral oil or silicone oil.

5. The drug dosage form of claim 1 wherein the compound—oil admixture is present within a capsule.

6. The drug dosage form of claim 1 wherein the compound—oil admixture is present within a soft shell capsule.

7. The drug dosage form of claim 1 wherein the compound—oil admixture is present within a specially sealed hard-shell capsule.

8. The drug dosage form of claim 1 wherein at least some of the compound—oil admixture is adsorbed on a pharmaceutically acceptable excipient.

9. The drug dosage form of claim 1 wherein the excipient having the compound—oil admixture adsorbed thereupon is within a capsule.

10. The drug dosage form of claim 1 wherein the excipient having the compound—oil admixture adsorbed thereupon is within a tablet.

11. A drug dosage form prepared by compression techniques comprising:
    a pharmaceutically acceptable excipient admixed with a substantially non-volatile pharmaceutically acceptable oil; and
    a compound susceptible to moisture-induced degradation treated with the pharmaceutically acceptable excipient to substantially waterproof the compound susceptible to moisture-induced degradation;
    wherein the drug dosage form is prepared by:
    (a) dispersing the compound susceptible to moisture-induced degradation in the pharmaceutically acceptable excipient;
    (b) compacting the compound susceptible to moisture-induced degradation into dosage forms using compression pressures of up to 5,000 psi/g.

12. The drug dosage form of claim 11 wherein the oil is an animal or vegetable oil.

13. The drug dosage form of claim 11 wherein said oil is olive, corn, peanut, nut, soy, rapeseed, cottonseed, vitamin E, fish, or tallow-derived oil.

14. The drug dosage form of claim 11 wherein the oil is a mineral oil or silicone oil.

15. The drug dosage form of claim 11 wherein the drug and the excipient—oil admixture are present within a capsule.

16. The drug dosage form of claim 11 wherein the drug and the excipient—oil admixture are present within a tablet.

17. A drug form prepared by compression techniques comprising:
    a compound susceptible to moisture-induced degradation treated with a first pharmaceutically acceptable oil to substantially waterproof the compound susceptible to moisture-induced degradation; and
    a pharmaceutically acceptable excipient admixed with a second pharmaceutically acceptable oil to substantially waterproof the pharmaceutically acceptable excipient, wherein the first pharmaceutical acceptable oil is different from the second pharmaceutically acceptable oil; the drug dosage form prepared by:
- (a) dispersing the compound susceptible to moisture-induced degradation in the pharmaceutically acceptable excipient;
- (b) compacting the compound susceptible to moisture-induced degradation into dosage forms using compression pressures of up to 5,000 psi/g.

18. The drug dosage form of claim 17 wherein the first pharmaceutically acceptable oil is an animal oil and the second pharmaceutically acceptable oil is a vegetable oil.

19. The drug dosage form of claim 17 wherein the first and the second pharmaceutically acceptable oils are, independently, olive, corn, peanut, nut, soy, rapeseed, cottonseed, vitamin E, fish, or tallow-derived oil.

20. The drug dosage form of claim 17 wherein the first pharmaceutically acceptable oil is an mineral oil and the second pharmaceutically acceptable oil is a silicone oil.

21. The drug dosage form of claim 17 wherein the compound—oil admixtured and the excipient—oil admixture are present within a capsule.

22. The drug dosage form of claim 17 wherein the compound—oil admixture and the excipient—oil admixture are present within a tablet.

23. A method for administering a compound susceptible to moisture-induced degradation to a patient comprising providing a unit dose of the compound which has not been processed employing high compression.

24. A method for administering a compound susceptible to moisture-induced degradation to a patient comprising providing a unit dose of the compound admixed with a substantially non-volatile, pharmaceutically acceptable oil.

25. The method of claim 24 wherein the compound—oil admixture is present within a capsule.

26. The method of claim 24 wherein the compound—oil admixture is adsorbed on a pharmaceutically acceptable excipient.

27. A method for administering a compound susceptible to moisture-induced degradation to a patient comprising providing a unit dose of the compound and a pharmaceutically acceptable excipient admixed with a substantially non-volatile, pharmaceutically acceptable oil.

28. A method for administering a compound susceptible to moisture-induced degradation to a patient comprising providing a unit dose of the compound and at least one pharmaceutically acceptable hydrophobic powder.

* * * * *